US005719049A

United States Patent [19]

Pellegrini et al.

[11] Patent Number: 5,719,049
[45] Date of Patent: Feb. 17, 1998

[54] PROCESS FOR PURIFYING HEPATITIS A VIRUS (HAV), VIRUS THUS PURIFIED AND VACCINE COMPOSITIONS CONTAINING IT

[75] Inventors: Vittoria Pellegrini; Nicoletta Fineschi, both of Siena, Italy; Arie J. Zuckerman, London, United Kingdom

[73] Assignee: Chiron S.p.A., Italy

[21] Appl. No.: 457,310

[22] Filed: Jun. 1, 1995

Related U.S. Application Data

[63] Continuation of Ser. No. 276,780, Jul. 18, 1994, Pat. No. 5,607,851, which is a continuation of Ser. No. 126,105, Sep. 22, 1993, abandoned, which is a continuation of Ser. No. 894,928, Jun. 8, 1992, abandoned.

[30] Foreign Application Priority Data

Jun. 18, 1991 [IT] Italy ............................ MI91A0166

[51] Int. Cl.$^6$ .................... C12N 7/00; A61K 39/29; A61K 39/02; C07K 1/00
[52] U.S. Cl. ..................... 435/235.1; 424/189.1; 424/226.1; 530/350
[58] Field of Search ................ 435/235.1; 530/350; 424/189.1, 226.1

[56] References Cited

U.S. PATENT DOCUMENTS

| | | | |
|---|---|---|---|
| 4,624,918 | 11/1986 | Herschberg | 435/68 |
| 4,673,634 | 6/1987 | Seto | 435/5 |
| 4,744,983 | 5/1988 | Morein | 530/419 |
| 5,004,688 | 4/1991 | Craig | 530/350 |
| 5,011,915 | 4/1991 | Yamazaki | 530/414 |
| 5,151,023 | 9/1992 | Kuzuhara | 428/89 |

FOREIGN PATENT DOCUMENTS

| | | |
|---|---|---|
| 0 171 086 A2 | 2/1986 | European Pat. Off. . |
| 0 171 765 A2 | 2/1986 | European Pat. Off. . |
| 0302692 | 2/1989 | European Pat. Off. . |
| 0 327 801 A1 | 8/1989 | European Pat. Off. . |

OTHER PUBLICATIONS

Flehmig, et al, 1989, "Immunogenicity of a Killed Hepatitis A Vaccine in Seronegative Volunteers" The Lancet, May 13, 1039–4041.

Welling, G.W. et al., "Isolation of Detergent–Extracted Sendai Virus Proteins by Gel–Filtration, Ion–Exchange and Reversed–Phase High–Performance Liquid Chromatography and the Effect on Immunological Activity", *J. of Chrom.,* 1984, 297, 101–109.

Flehmig, B. et al., "Immunogenicity of a Hepatitis A Virus Vaccine", *J. of Medical Virology* 1987, 22, 7–16.

Locarnini, S. et al., "Purification of Hepatitis A Virus from Human Feces", *Intervirology* 1978, 10, 300–308.

Provost, P.J. et al., "An Inactivated Hepatitis A Viral Vaccine of Cell Culture Origin", *J. of Med. Virology* 1986, 19, 23–31.

*Primary Examiner*—Lynette F. Smith
*Attorney, Agent, or Firm*—Woodcock,Washburn,Kurtz, et al.; Barbara G. McClung; Robert P. Blackburn

[57] ABSTRACT

A process is described for the purification or the hepatitis A virus, which allows one to obtain with good yields a pure product, in which organic material collected by centrifugation after lysis or the culture cells is submitted to gel filtration and successively to ion exchange chromatography.

3 Claims, No Drawings

PROCESS FOR PURIFYING HEPATITIS A VIRUS (HAV), VIRUS THUS PURIFIED AND VACCINE COMPOSITIONS CONTAINING IT

This is a continuation of application Ser. No. 08/276,780, filed on Jul. 18, 1994, U.S. Pat. No. 5,609,851 which is a continuation of Ser. No. 08/126,105, now abandoned filed on Sep. 22, 1993, which is a continuation of Ser. No. 07/894,928, filed Jun. 8,1992 now abandoned.

INVENTION FIELD

A process is described for the purification of the hepatitis A virus (HAV) in which the material from the culture cells, after cell lysis and centrifugation, is submitted to gel filtration and the thus obtained eluate is submitted to ion exchange chromatography.

STATE OF THE ART

The hepatitis A virus (HAV) is a icosahedral morphology Picornavirus with 32 capsomeres on its surface, which presents four important structural polypeptides: VP1 with a molecular weight MSW 30.000–33.000, VP2 24.000–27.000, VP3 21.000–23.000, VP4 7.000–14.000.

Said four proteins are the ones responsible for the antigenic virus power and are therefore the ones which the purification processes tend to put in evidence and to isolate in order to obtain, with a good degree of purity, an inactivated vaccine. The purification processes seek to eliminate cellular contaminants and growth factors which are employed in the virus production process.

Various methods for the partial virus purification, both for vaccination and for virus characterization purposes, have been described. For example, through the virus sedimentation by means of a 20% sucrose pad and successive centrifugation in a cesium chloride gradient [P. J. Provost et al. J. of Medical Virology 19, p. 23–31 (1986)], through ammonium sulphate precipitation and sedimentation with a 20% sucrose pad and cesium chloride gradient [Flehmig B. et al., J. of Medical Virology 22, p. 7–16 (1987)], with a lysis buffer, freezing, defrosting, sonication to set the virus free, ultrafiltration with tangential flow and purification in cesium chloride gradient [Flehmig et al., The Lancet, May 13, p. 1039 (1989)], through various clarification cycles and successive freon or chloroform extraction followed by gel filtration, ion exchange chromatography and purification in cesium chloride gradient [S. A. Locarnini, Intervirology 10, 300–308 (1978)].

All the above mentioned processes employ, at least in one step, ultracentrifugation systems and high cost materials such as cesium chloride, and therefore, although yielding excellent results on a small scale, are hardly suitable for an industrial production, in which process duration, costs and availability of suitable personnel have to be taken into consideration. In the European Patent Application EP-A-302692 a process for the purification of hepatitis A virus is described, which employs sonication for the cell lysis, followed by extraction with organic solvents and successive concentration, chromatography on anion exchange resins and, finally, gel filtration chromatography. Also this process, particularly in view of the use of sonication and of organic phase extractions and concentrations, presents, on an industrial scale, certain operative difficulties.

DETAILED DESCRIPTION OF THE INVENTION

The process according to the present invention allows to obviate the mentioned drawbacks and is therefore a valid contribution to the purification on an industrial scale and the production of a purified HAV virus suitable for the use as a vaccine.

Diploid human cells MRC-5 designated by the World Health Organization as suitable for the production of vaccines for human use, cultivated and collected according to conventional techniques, were used.

The cells were infected with HAV at the 30th passage. After 21 days incubation, the cell substrate was washed with PBS-A to eliminate as much as possible the fetal bovine serum present in the culture medium and indispensable for the substrate. The infected cells were taken up with trypsin EDTA following traditional methods and re-suspended in hypotonic buffer (Tris 10 mM, NaCl 10 mM, pH 7.5), this causing cell lysis and therefore setting the virus free, and frozen.

At the time of purification the material is defrosted and treated with 2% Triton-X-100 for 30 min. at room temperature, stirring about every 5 min.; the material is then collected by centrifugation, so as to remove the cell fragments; this treatment allows the solubilization of membrane lipids with which the virus is strictly associated. The next step is gel filtration, employing gel filtration beds of both agarose and dextran, e.g. SEPHAROSE CL-4B resin (Pharmacia) equilibrated in TNE buffer (Tris 10 mM, NaCl 150 mM, EDTA 1 mM, pH 7.2–7.6), containing 0.1–0.2% Triton-X-100 or glycine buffer 0.1M with 0.2% deoxycholate, pH 8.5. The eluated material is collected in 20 ml fractions which are tested for the presence of HAV by an ELISA assay. With this passage, yields of 85–95% are obtained with an approximate eight-fold purity increase (30–50 μg virus per mg of protein).

The eluate obtained in the preceding step is then submitted to ion exchange chromatography employing anion exchange resins, such as e.g. DEAE SEPHAROSE CL-6B resin equilibrated in TNE containing 0.1%–0.2% Triton-X-100; in these conditions the virus is adsorbed on the bed while part of the contaminants are not retained.

After washing the column with TNE, to eliminate the detergent, eluition is performed decreasing the pH and increasing the ion strength. To this end a phosphate buffer may be employed with a continuous pH gradient from 7.4 to 4 and ionic strength from 0 to 0.3M NaCl. The yield in this second step is of the order of 50% with respect to the preceding step and the purity of the collected virus is increased 6 to 10 times (with an average virus contents of 70% on the total protein). The thus purified material is filtered on a membrane of 0.22 μm porosity and inactivated with 1:2000 formalin at 35° C. for 5 days under continuous stirring.

During the inactivation period, disaggregating treatments are performed, the 2nd day the material is sonicated at 50–60 W 1 sec/ml. The third day the material is filtered on a 0.22 μm membrane and L-lysine.HCl 25 mM is added. After inactivation, the suspension is dialyzed against PBS A (1:100 v/v) for about 36 hrs, with an intermediate buffer substitution. After dialysis, the material is submitted to a sterilizing filtration and the product undergoes all the required controls: sterility, pyrogenicity, inactivation, antigenicity, pH, stability, residual formalin.

EXPERIMENTAL SECTION

MRC-5 cells at the 30th passage in rotating 850 $cm^2$ bottles are infected with HAV (strain LSH/S ATCC VR 2266) at a 0.5 MOI. After a 20 day incubation period, the cellular substrate is washed 3 times with serum-free medium maintaining the last washing overnight. The following day the cells are removed with tripsine-EDTA following traditional methods, and suspended again in hypotonic buffer (Tris 10 mM, NaCl 10 mM, pH 7.5) 1 ml for each 100 cm$^2$ cell culture and frozen.

60 ml of the frozen suspension, deriving from approximately 5.700 cm$^2$ culture are defrosted and treated with a non ionic detergent (2% Triton-X-100) for 20 to 30 minutes at room temperature under moderate stirring every 5–10 minutes. The sample is centrifuged at 400 g for 10 minutes while cooling to remove cellular fragments. The supernatant is purified through gel filtration on a agarose resin (SEPHAROSE CL4B resin Pharmacia)column 5×90 cm (K 50/100 column, Pharmacia) equilibrated with Tris 10 mM, NaCl 150 mM, EDTA 1 mM buffer, pH 7.4, containing 0.1% Triton-X-100 at a 75 ml/h flow rate. The eluted material is collected in 20 ml fractions which are tested for the presence of HAV by a ELISA assay. The HAV containing fractions are collected, obtaining approximately 400 ml. This material is further purified by ion exchange chromatography seeding about 200 ml, at a flow rate of 100 ml/h on a anionic resin (SEPHAROSE CL6B resin Pharmacia) column 5×5 (column XK 50/30 Pharmacia) which had previously been equilibrated in Tris 10 mM, NaCl 150 mM, EDTA 1 mM, pH 7.4 buffer containing 0.1% Triton-X-100. Under such conditions the virus is adsorbed on the matrix. The matrix is washed with Triton-X-100 free buffer to remove the detergent and the virus is eluted at a flow of approximately 160 ml/h, applying a continuous pH gradient and ionic strength, starting from pH 7.4 and NaCl 0 mM to pH 4 and NaCl 10.3M. The eluted material is collected in fractions of about 10 ml and the fractions found positive for the presence of HAV at a ELISA assay are put together.

A virus content of 70% on the total protein is thus obtained. The thus purified material is filtered on 0.22 μm porous membrane and inactivated with formalin 1.2000 at 35° C. for 5 days under continuous stirring. During the inactivation period, disaggregation treatments are performed: on the 2nd day the material is sonicated at 50–60 W per 1 second/1 ml; on the 3rd day it is filtered on a 0.22 μm membrane and L-lysine.HCl 25 mM is added. After inactivation, the suspension is dialyzed against PBS-A (KCl 2.7 mM, KH$_2$PO$_4$ 1.5 mM, NaCl 137 mM, NaH$_2$PO$_4$ 8.1 mM, pH 7.4) in a 1:100 v/v ratio for 36 hours with an intermediate buffer substitution. After dialysis, the material undergoes a sterilizing filtration and is then submitted to the usual controls for sterility, pyrogenicity, inactivation, antigenicity, pH, stability and residual formalin.

Hepatitis A virus, strain LSH/H, purified as outlined above was deposited with the American Type Culture Collection (ATCC),12301 Parklawn Dr., Rockville, Md., 20852, on Oct. 24, 1989. The deposit was made pursuant to the Budapest Treaty. The deposit was assiged ATCC accession number VR2266.

What is claimed is:

1. Hepatitis A virus (HAV) strain LSH/S deposited as ATCC VR 2226.

2. HAV virus purified and inactivated, obtained according to the process as follows:
    a) lysing cells infected with HAV strain LSH/S in the presence of a first concentration of detergent;
    b) removing cell fragments to produce a supernatant;
    c) performing gel filtration of the supernatant in the presence of a second concentration of detergent;
    d) submitting the eluate obtained in step c) to ion exchange chromatography; and
    e) eluting the virus adsorbed in step d) using a detergent-free elution buffer.

3. A vaccine composition containing the virus according to claim 2.

* * * * *

UNITED STATES PATENT AND TRADEMARK OFFICE
CERTIFICATE OF CORRECTION

PATENT NO. : 5,719,049
DATED : February 17, 1998
INVENTOR(S) : Pellegrini et al.

It is certified that error appears in the above-indentified patent and that said Letters Patent is hereby corrected as shown below:

In the Abstract, line 4, please delete "or" and insert therefor --of--.

Col. 3, line 2, please delete "tripsine" and insert therefor --trypsin--.

Col. 3, line 31, please delete "10.3M" and insert therefor --0.3M--.

Col. 4, line 17, please delete "assiged" and insert therefor --assigned--.

Col. 4, line 21, please delete "2226" and insert therefor --2266--.

Signed and Sealed this

Seventh Day of September, 1999

Q. TODD DICKINSON

Attest:

Attesting Officer    Acting Commissioner of Patents and Trademarks